United States Patent
Imai et al.

(10) Patent No.: US 7,479,563 B2
(45) Date of Patent: Jan. 20, 2009

(54) METHOD OF PRODUCING POLYMORPHIC CRYSTALS OF DONEPEZIL HYDROCHLORIDE

(75) Inventors: Akio Imai, Ibaraki (JP); Akihiko Shimotani, Ibaraki (JP)

(73) Assignee: Eisai R&D Management Co., Ltd., Bunkyo-ku (JP)

( * ) Notice: Subject to any disclaimer, the term of this patent is extended or adjusted under 35 U.S.C. 154(b) by 633 days.

(21) Appl. No.: 11/113,077

(22) Filed: Apr. 25, 2005

(65) Prior Publication Data
US 2005/0209281 A1 Sep. 22, 2005

Related U.S. Application Data

(63) Continuation of application No. 10/380,780, filed as application No. PCT/JP01/08057 on Sep. 17, 2001, now abandoned.

(30) Foreign Application Priority Data

Sep. 25, 2000 (JP) ............................ 2000-289956
Oct. 23, 2000 (JP) ............................ 2000-322184

(51) Int. Cl.
*C07D 211/32* (2006.01)
*A61K 31/445* (2006.01)

(52) U.S. Cl. ...................... 546/206; 546/205; 514/315
(58) Field of Classification Search ................ 514/315; 546/205, 206
See application file for complete search history.

(56) References Cited

U.S. PATENT DOCUMENTS 5,985,864 A 11/1999 Imai et al. .................... 546/206
6,140,321 A 10/2000 Imai et al. .................... 546/206

FOREIGN PATENT DOCUMENTS

JP 10-53576 A 2/1998
WO 97/46526 A1 12/1997

OTHER PUBLICATIONS

US Pharmacopia #23, conditional formulary #18, (1955), p. 1843-1844.
RN120011-70-3, (1967).
RN2083-87-6, (1967).

*Primary Examiner*—Celia Chang
(74) *Attorney, Agent, or Firm*—Birch, Stewart, Kolasch & Birch, LLP

(57) ABSTRACT

The present invention provides a simple method of producing polymorphic crystal (III), which has high safety to environment and the bodies of operators; is gentle to environment; and can produce at low costs; and has a high refining effect. It is a method of producing polymorphic crystal (III) of donepezil hydrochloride (chemical name: 1-benzyl-4-[(5,6-dimethoxy-1-indanon)-2-yl]methylpiperidine•monohydrochloride) represented by the following structural formula (formula (I)), which comprises dissolving donepezil (chemical name: 1-benzyl-4-[(5,6-dimethoxy-1-indanon)-2-yl]methylpiperidine) in ethanol; and adding hydrochloric acid or hydrogen chloride thereto, followed by stirring.

5 Claims, No Drawings

US 7,479,563 B2

METHOD OF PRODUCING POLYMORPHIC CRYSTALS OF DONEPEZIL HYDROCHLORIDE

This application is a Continuation of application Ser. No. 10/380,780, filed on Mar. 18, 2003 now abandoned, and for which priority is claimed under 35 U.S.C. § 120. This application also claims priority of Application No. PCT/JP01/08057 filed in JAPAN on Sep. 17, 2001 under 35 U.S.C. § 119. Further, under the provisions of 35 U.S.C. § 119, this application claims priority to Patent Application Nos. 2000-289956 and 2000-322184, filed in Japan on Sep. 25, 2000 and Oct. 23, 2000, respectively. The entire contents of all are hereby incorporated by reference.

FIELD OF THE INVENTION

The present invention relates to a method of industrially producing a highly stable polymorphic crystal (III) of donepezil hydrochloride (chemical name: 1-benzyl-4-[(5,6-dimethoxy-1-indanon)-2-yl] methylpiperidine•monohydrochloride) which is disclosed in JP-A 10-53576 (WO-A 97-46527) and has a superior effect as medicines.

PRIOR ART

Donepezil hydrochloride has an acetylcholinesterase inhibitory action and is useful as an agent for treating, preventing or improving various senile dementia especially Alzheimer-type senile dementia, cerebrovascular disorder associated with cerebral apoplexy (cerebral hemorrhage and cerebral infarction), cerebral arteriosclerosis, head injury etc., attention-deficit, logopathy, hypobulia, attention deficit hyperactivity disorders, emotional disorders, memorization disorders, paranoid hallucinatory states, abnormal behavior etc. associated with sequelae of encephalitis, cerebral paralysis etc., etc.

This agent is mostly administered for a long period of time in the forms of oral solid formulations such as tablets, capsules and granules, percutaneous absorption formulations such as ointments, tapes and suppositories, and injections. The storage stability of the agent in the course of distribution and in hospitals and homes is therefore important. Particularly, in the case of oral solid formulations prepared by mixing original drug put in a powder state with various additives, the selection of polymorphic crystal of the original drug having superior physical properties including stability is important.

In JP-A 10-53576, five types of polymorphic crystal ((I), (II), (III), (IV) and (V)) having high stability and the physical properties thereof are disclosed. It is shown that, particularly, the polymorphic crystal (III) has the following superior characteristics to the other crystal forms: (1) it has a lower water content and does not absorb moisture until relative humidity reaches 96.6% (25° C., two weeks) and (2) an increase in the amount of HPLC impurities is not observed when it is stored at 80° C. for two weeks. Also, as a method of producing the polymorphic crystal (III) of donepezil hydrochloride, a method in which using donepezil, hydrochlorination and crystallization are carried out either simultaneously or successively (the following methods 1) to 9)) and a method in which an amorphous or various polymorphic crystals of donepezil hydrochloride is used to carry out crystallization of the polymorphic crystal (III) (the following methods 10) to 18)) are disclosed.

Production method in which hydrochlorination and crystallization of the polymorphic crystal (III) are carried out either simultaneously or successively by using donepezil (JP-A 10-53576)
1) Donepezil is dissolved in acetone, to which is added hydrochloric acid or hydrogen chloride.
2) Donepezil is dissolved in ethyl acetate, to which is added hydrochloric acid or hydrogen chloride.
3) Donepezil is dissolved in ethanol, to which is added hydrochloric acid or hydrogen chloride, and then is added one solvent selected from diethyl ether, isopropyl ether or n-hexane.
4) Donepezil is dissolved in methanol, to which is added hydrochloric acid or hydrogen chloride, and then is added acetone.
5) Donepezil is dissolved in ethanol, to which is added hydrochloric acid or hydrogen chloride, and then is added t-butyl methyl ether.
6) Donepezil is dissolved in acetonitrile, acetone, hydrate acetone, tetrahydrofuran or N,N-dimethylformamide, to which is added hydrochloric acid or hydrogen chloride.
7) Donepezil is dissolved in ethyl acetate, to which is added hydrochloric acid or hydrogen chloride, and then is added t-butyl methyl ether.
8) Donepezil is dissolved in dimethylsulfoxide, to which is added hydrochloric acid or hydrogen chloride, and then is added t-butyl methyl ether.
9) Donepezil is dissolved in toluene, to which is added hydrochloric acid or hydrogen chloride.

Production method in which crystallization of the polymorphic crystal (III) is carried out using amorphous or various polymeric crystals of donepezil hydrochloride (JP-A 10-53576)
10) Donepezil hydrochloride is dissolved in ethanol, to which is added diethyl ether.
11) Donepezil hydrochloride is dissolved in methylene chloride, to which is added n-hexane.
12) The polymorphic crystal (I) or (II) of donepezil hydrochloride is heated.
13) Donepezil hydrochloride is recrystallized from methanol at 10° C. or more.
14) Donepezil hydrochloride is dissolved in methanol, to which is added t-butyl methyl ether or acetonitrile.
15) Donepezil hydrochloride is dissolved in ethanol, to which is added t-butyl methyl ether or acetonitrile, followed by stirring at 10° C. or more.
16) Donepezil hydrochloride is dissolved in N,N-dimethylformamide or dimethylsulfoxide, to which is then added t-butyl methyl ether.
17) Donepezil hydrochloride is recrystallized from isopropyl alcohol.
18) The polymorphic crystal (I), (II), (IV) or (V) of donepezil hydrochloride or amorphous donepezil hydrochloride is stirred in a solvent such as methanol, ethanol, ethyl acetate or acetone, and converted.

However, the methods 1) to 9) in which using donepezil, hydrochlorination and crystallization of the polymolphic crystal (III) are carried out either simultaneously or successively in a solvent use, as a solvent, 1) acetone, 2) ethyl acetate, 3) one solvent selected from diethyl ether, isopropyl ether and n-hexane, 4) acetone, 5) t-butyl methyl ether, 6) acetonitrile, acetone, hydrate acetone, tetrahydrofuran or N,N-dimethylformamide, 7) ethyl acetate and t-butyl methyl ether, 8) dimethylsulfoxide and t-butyl methyl ether, and 9) toluene, respectively. These methods therefore have the problems concerning flammability based on high volatility of organic solvents, safety to environment and the health of operators and solvents remaining in the produced donepezil hydrochloride crystal and the like.

Also, the methods 10) to 18) (excluding the method (12)) in which using amorphous donepezil hydrochloride or various polymorphic crystals of donepezil hydrochloride, the crystallization of the polymorphic crystal (III) is carried out also use, as a solvent, 10) diethyl ether, 11) methylene chloride and n-hexane, 13) methanol, 14) methanol and t-butyl methyl ether or acetonitrile, 15) t-butyl methyl ether or acetonitrile, 16) N,N-dimethylformamide or dimethylsulfoxide and t-butyl methyl ether, 17) isopropyl alcohol and 18) methanol, ethyl acetate or acetone and the like. These methods therefore have the same problems as above.

It is to be noted that the production method 12) in which "the polymorphic crystals (I) or (II) of donepezil hydrochloride is heated" poses many problems as an industrial production method because decomposition is accelerated in a heating step and it is therefore difficult to secure chemical stability.

Also, in 18), a method in which the polymorphic crystal (I), (II), (IV) or (V) of donepezil hydrochloride or amorphous donepezil hydrochloride is stirred in ethanol which is a highly safe solvent is also disclosed. However, no simple method for preparing the polymorphic crystal (III) of donepezil hydrochloride directly from donepezil has been developed yet.

A simple method of producing the polymorphic crystal (III) which method has high safety to environment and the bodies of operators, is gentle to environment, can produce at low costs and is excellent in refining effect has been desired much as the method of the production of the polymorphic crystal (III).

Particularly, "a method of producing the polymorphic crystal (III) which can produce the polymorphic crystal (III) of donepezil hydrochloride directly from donepezil" has been sought, which is a method of producing the polymorphic crystal (III) fulfilling these requirements and is a simpler process.

DISCLOSURE OF THE INVENTION

In the above situation, the inventors of the present invention have made earnest studies and as a result, found that the intended object can be attained by the structure shown below, and they completed the present invention.

The present invention is a method of producing polymorphic crystal (III) of donepezil hydrochloride (chemical name: 1-benzyl-4-[(5,6-dimethoxy-1-indanon)-2-yl]methylpiperidine•monohydrochloride) represented by the following structural formula (formula (I)), which comprises dissolving donepezil (chemical name: 1-benzyl-4-[(5,6-dimethoxy-1-indanon)-2-yl]methylpiperidine) in ethanol; adding hydrochloric acid or hydrogen chloride thereto; and stirring. The synthetic flow according to the present invention is shown in the (formula 2). Ethanol used to dissolve donepezil may be either pure ethanol or denatured ethanol.

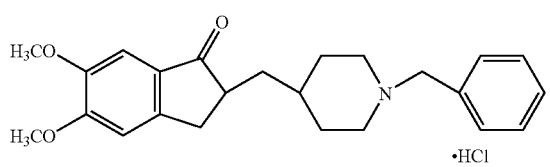

(Formula 1)

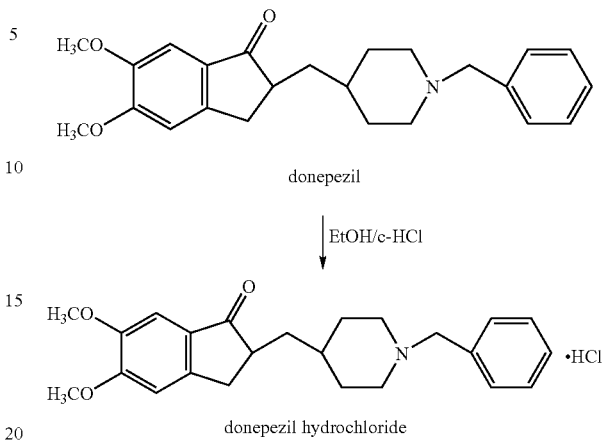

In JP-A10-53576, the presence of polymorphic crystals (I), (II), (III), (IV) and (V) is disclosed. It is clarified that each has its intrinsic powder X-ray diffraction pattern, infrared absorption spectrum and melting point, and is largely different in physical properties. Especially, it is also shown that the polymorphic crystal (III) has more marked characteristics than other crystal types: specifically it has smaller hygroscopicity and higher heat stability.

That is, it provides the method of producing polymorphic crystal (III) of donepezil hydrochloride according to claim 1 or 2, wherein the polymorphic crystal (III) of donepezil hydrochloride is a crystal having peaks at the following diffraction angles expressed as 2θ in its powder X-ray diffraction patterns:

TABLE 3

| Diffraction angle (2θ°) | Intensity (I/Io) |
| --- | --- |
| 6.56 | 30 |
| 9.94 | 8 |
| 13.00 | 17 |
| 15.00 | 47 |
| 15.26 | 14 |
| 15.74 | 6 |
| 16.48 | 35 |
| 17.42 | 4 |
| 18.10 | 21 |
| 18.50 | 56 |
| 19.50 | 17 |
| 20.10 | 32 |
| 20.94 | 21 |
| 21.66 | 100 |
| 22.32 | 25 |
| 22.92 | 17 |
| 23.92 | 19 |
| 24.68 | 17 |
| 26.00 | 44 |
| 27.20 | 23 |
| 28.02 | 29 |
| 28.22 | 40 |
| 28.60 | 13 | and absorption at the following wave numbers in its infrared absorption spectrum in potassium bromide: 559, 641, 648, 702, 749, 765, 786, 807, 851, 872, 927, 949, 966, 975, 982, 1007, 1034, 1071, 1080, 1111, 1119, 1131, 1177, 1190, 1205, 1217, 1230, 1250, 1265, 1292, 1313, 1367, 1389, 1420, 1438, 1453, 1461, 1470, 1500, 1589, 1605, 1697, 2407, 2419, 2461, 2624, 2641, 2651, 2667, 2837, 2848, 2873, 2924, 2954, 2961, 2993, 3007, 3377 and 3433 cm$^{-1}$, or a polymorphic crystal having peaks at the following diffraction angles expressed as 2θ in its powder X-ray diffraction patterns:

TABLE 4

| Diffraction angle (2θ°) | Intensity (I/Io) |
| --- | --- |
| 6.48 | 21 |
| 9.84 | 7 |
| 12.96 | 19 |
| 14.94 | 45 |
| 15.20 | 13 |
| 16.44 | 31 |
| 18.04 | 20 |
| 18.46 | 55 |
| 19.44 | 17 |
| 20.02 | 30 |
| 20.86 | 20 |
| 21.02 | 13 |
| 21.58 | 100 |
| 22.22 | 23 |
| 22.90 | 15 |
| 23.92 | 13 |
| 24.64 | 15 |
| 25.92 | 40 |
| 26.18 | 17 |
| 27.14 | 21 |
| 28.14 | 37 |
| 28.56 | 11 |
| 29.94 | 12 | and absorption at the following wave numbers in its infrared absorption spectrum in potassium bromide: 558.3, 641.1, 702.4, 748.5, 765.0, 786.1, 807.3, 850.8, 872.0, 926.8, 974.9, 1034.1, 1071.5, 1111.6, 1190.1, 1216.6, 1265.4, 1291.9, 1312.9, 1364.4, 1420.2, 1438.1, 1458.8, 1499.1, 1522.2, 1542.6, 1560.1, 1570.2, 1589.1, 1638.8, 1647.8, 1654.3, 1697.3, 1718.1, 1734.5, 1751.4, 1773.7, 1793.5, 1845.8, 2345.3, 2461.6, 2924.2 and 3447.9 cm$^{-1}$. The melting point of the polymorphic crystal (III) is 229 to 231° C. (decomposed).

Further, the present invention is a method of producing polymorphic crystal (III) of donepezil hydrochloride, which comprises dissolving donepezil in ethanol; adding hydrochloric acid or hydrogen chloride thereto; stirring; and then collecting by filtration and drying the crystals.

In the present invention, the amount of ethanol used as the crystallizing solvent is not particularly limited, however, the amount is preferably 3 to 20 parts by weight, more preferably 3 to 15 parts by weight and still more preferably 3 to 10 parts by weight to one part by weight of donepezil.

Although no particular limitation is imposed on the internal temperature (crystallization temperature) of the solvent when stirring after donepezil is dissolved in ethanol and hydrochloric acid or hydrogen chloride is added, the temperature is generally 10 to 40° C., preferably 15 to 35° C. and more preferably 20 to 30° C. It is desirable to stir with keeping that internal temperature. This makes it possible to produce polymorphic crystal (III) of donepezil hydrochloride which is reduced in the amount of the residual solvent (ethanol), and has a small particle diameter and a small 90% volume cumulative diameter in the particle size distribution in a high yield.

The particle size distribution of the polymorphic crystal (III) of donepezil hydrochloride produced in the present invention is affected also by stirring speed and stirring time besides the crystallization temperature, and varies with time during crystallization. Specifically, in the crystallizing step, crystals having a double-peak type particle size distribution first precipitates. When the stirring is continued, the coagulate falls to small pieces and the resulting crystals has a small diameter, showing a particle size distribution with a single peak. It is therefore desirable to increase stirring speed and/or to set a baffle plate in a reactor to carry out stirring, to thereby accelerate the collapse of the coagulate.

It is generally preferable that the stirring speed be 10 to 1000 m/min in terms of line speed, though it differs depending on the size of the reactor (apparatus).

When donepezil is dissolved in ethanol, hydrochloric acid or hydrogen chloride is added thereto and the mixture is stirred, the precipitation of polymorphic crystal of donepezil hydrochloride starts immediately. In order to obtain the polymorphic crystal (III) of donepezil hydrochloride in a high yield, it is necessary to take a plenty time for allowing the system to stand with stirring after the precipitation of crystals starts. It is desirable to continue stirring for at least one hour after the precipitation of crystal starts.

Also, a process may be adopted in which after hydrochloric acid or hydrogen chloride is added, the system is stirred under keeping the internal temperature at 10 to 40° C., and then cooled to 0° C. or more and less than 10° C. on and after one hour passes after the precipitation of crystal starts. This cooling operation ensures that the polymorphic crystal (III) can be obtained in a high yield.

Moreover, in the present invention, polymorphic crystal (III) of donepezil hydrochloride may be added as seed crystals to the system and stirred, after donepezile is dissolved in ethanol and hydrochloric acid or hydrogen chloride is added thereto. The amount of the polymorphic crystal (III) of donepezil hydrochloride to be added as the seed crystals is usually 0.01 to 10% by weight, preferably 0.01 to 5% by weight and particularly preferably 0.1 to 1% by weight to one part by weight of donepezil.

The residual solvent in the polymorphic crystal (III) obtained by the method of producing polymorphic crystal (III) of donepezil hydrochloride according to the present invention and the waste solvent generated in the production steps are only ethanol having almost no safety problem, and also the amount of these solvents is very small. Therefore, it is superior in safety to a patient who takes the product and to operators, and also in safety to working environment. Also, it has the effect of improving qualities from a viewpoint of the residual solvents.

In addition, the production method according to the present invention has the effect of refining donepezil and therefore polymorphic crystal (III) of donepezil hydrochloride with high purity can be produced.

In the present invention, the polymorphic crystal (III) of donepezil hydrochloride may be produced using, for example, the following method.

1 kg of donepezil is dissolved by stirring in 6.4 kg of ethanol under heating, followed by adding 302 g of concentrated hydrochloric acid thereto. Then, it is continued stirring while keeping the internal temperature at about 10 to 40° C. After the precipitation started, the mixture is stirred at the internal temperature of about 10 to 40° C. for 18 hours and then cooled to the internal temperature of 9° C. The crystals are collected by filtration and dried about 5 hours after the cooling is started, to produce polymorphic crystal (III) of donepezil hydrochloride.

EXAMPLES

The present invention will be further explained in more detail by way of the following Examples, which, however, are not intended to be limiting of the present invention.

Example 1

50 g of donepezil was dissolved by stirring in 315 g of ethanol under heating, followed by adding 15.1 g of concentrated hydrochloric acid thereto at the internal temperature of 30° C. Then, it was cooled and continued stirring while keeping the internal temperature at 30° C. Crystals started precipitating about 30 minutes after the concentrated hydrochloric acid was poured into the mixture. After the precipitation started, the mixture was stirred at the internal temperature of 15° C. for 18 hours and then cooled to the internal temperature of 9° C. The crystals were collected by filtration and dried about 4 hours after the cooling was started, to give 52.32 g of polymorphic crystal (III) of donepezil hydrochloride (yield: 95.5%).

Example 2

50 g of donepezil was dissolved by stirring in 240 g of ethanol under heating, followed by adding 15.1 g of concentrated hydrochloric acid thereto at the internal temperature of 30° C. Then, it was cooled and continued stirring while keeping the internal temperature at about 25° C. Crystals started precipitating about 1 hour after the concentrated hydrochloric acid was poured into the mixture. After the precipitation started, the mixture was stirred at the internal temperature of 25° C. for 17 hours and then cooled to the internal temperature of 9° C. The crystals were collected by filtration and dried about 3 hours after the cooling was started, to give 52.25 g of polymorphic crystal (III) of donepezil hydrochloride (yield: 95.3%).

Example 3

50 g of donepezil was dissolved by stirring in 320 g of ethanol under heating, followed by adding 15.1 g of concentrated hydrochloric acid thereto at the internal temperature of 30° C. After concentrated hydrochloric acid was poured, 100 mg of seed crystals were added. The mixture was cooled and continued stirring while keeping the internal temperature at about 20° C. Crystals started precipitating immediately after the seed crystals were added. After the precipitation started, the mixture was stirred at the internal temperature of 20° C. for 18 hours and then cooled to the internal temperature of 9° C. The crystals were collected by filtration and dried about 3 hours after the cooling was started, to give 52.90 g of polymorphic crystal (III) of donepezil hydrochloride (yield: 96.5%).

Example 4

50 g of donepezil was dissolved by stirring in 280 g of ethanol under heating, followed by adding 15.1 g of concentrated hydrochloric acid thereto at the internal temperature of 28° C. Then, it was cooled and continued stirring while keeping the internal temperature at about 25° C. Crystals started precipitating about 40 minutes after the concentrated hydrochloric acid was poured into the mixture. After the precipitation started, the mixture was stirred at the internal temperature of 25° C. for 18 hours and then cooled to the internal temperature of 9° C. The crystals were collected by filtration and dried about 4 hours after the cooling was started, to give 52.81 g of polymorphic crystal (III) of donepezil hydrochloride (yield: 96.4%).

Example 5

30 g of donepezil was dissolved by stirring in 360 g of ethanol under heating, followed by adding 9 g of concentrated hydrochloric acid thereto at the internal temperature of 30° C.

Then, it was cooled and continued stirring while keeping the internal temperature at about 25° C. Crystals started precipitating about 2 hours after the concentrated hydrochloric acid was poured into the mixture. After the precipitation started, the mixture was stirred at the internal temperature of 25° C. for 17 hours and then cooled to the internal temperature of 9° C. The crystals were collected by filtration and dried about 4 hours after the cooling was started, to give 30.85 g of polymorphic crystal (III) of donepezil hydrochloride (yield: 93.8%).

Example 6

50 g of donepezil was dissolved by stirring in 320 g of ethanol under heating, followed by adding 15.1 g of concentrated hydrochloric acid thereto at the internal temperature of 30° C.

Then, it was cooled and continued stirring while keeping the internal temperature at about 25° C. Crystals started precipitating about 30 minutes after the concentrated hydrochloric acid was poured into the mixture. After the precipitation started, the mixture was stirred at the internal temperature of 25° C. for 18 hours and then cooled to the internal temperature of 9° C. The crystals were collected by filtration and dried about 48 hours after the cooling was started, to give 52.47 g of polymorphic crystal (III) of donepezil hydrochloride (yield: 95.7%).

Example 7

50 g of donepezil was dissolved by stirring in 320 g of ethanol under heating, followed by adding 15.1 g of concentrated hydrochloric acid thereto at the internal temperature of 30° C.

Then, it was cooled and continued stirring while keeping the internal temperature at about 25° C. Crystals started precipitating about 1 hour after the concentrated hydrochloric acid was poured into the mixture. After the precipitation started, the mixture was stirred at the internal temperature of 25° C. for 22 hours. Then, the crystals were collected by filtration and dried, to give 51.28 g of polymorphic crystal (III) of donepezil hydrochloride (yield: 93.6%).

Example 8

50 g of donepezil was dissolved by stirring in 320 g (400 ml) of ethanol under heating, followed by adding 15.1 g of concentrated hydrochloric acid thereto at the internal temperature of 30° C. Then, it was cooled and continued stirring while keeping the internal temperature at about 20° C. Crystals started precipitating about 30 minutes after the concentrated hydrochloric acid was poured into the mixture. After the precipitation started, the mixture was stirred at the internal temperature of 20° C. for 18 hours and then cooled to the internal temperature of 9° C. The crystals were collected by filtration and dried about 5 hours and a half after the cooling was started, to give 52.3 g of polymorphic crystal (III) of donepezil hydrochloride (yield: 95.4%).

Example 9

50 g of donepezil was dissolved by stirring in 320 g of ethanol under heating, followed by adding 15.1 g of concentrated hydrochloric acid thereto at the internal temperature of 30° C.

Then, it was cooled and continued stirring while keeping the internal temperature at about 25° C. Crystals started precipitating about 30 minutes after the concentrated hydrochloric acid was poured into the mixture. After the precipitation started, the mixture was stirred at the internal temperature of 25° C. for 18 hours and then cooled to the internal temperature of 9° C. The crystals were collected by filtration and dried about 4 hours after the cooling was started, to give 52.5 g of polymorphic crystal (III) of donepezil hydrochloride (yield: 95.8%).

Example 10

50 g of donepezil was dissolved by stirring in 320 g of ethanol under heating, followed by adding 15.1 g of concentrated hydrochloric acid thereto at the internal temperature of 32° C.

Then, it was cooled and continued stirring while keeping the internal temperature at about 30° C. Crystals started precipitating about 30 minutes after the concentrated hydrochloric acid was poured into the mixture. After the precipitation started, the mixture was stirred at the internal temperature of 30° C. for 17 hours and then cooled to the internal temperature of 9° C. The crystals were collected by filtration and dried about 5 hours after the cooling was started, to give 52.74 g of polymorphic crystal (III) of donepezil hydrochloride (yield: 96.2%).

Example 11

50 g of donepezil was dissolved by stirring in 320 g of ethanol under heating, followed by adding 15.1 g of concentrated hydrochloric acid thereto at the internal temperature of 35° C.

It was continued stirring while keeping the internal temperature at about 35° C. Crystals started precipitating about 1 hour and a half after the concentrated hydrochloric acid was poured into the mixture. After the precipitation started, the mixture was stirred at the internal temperature of 35° C. for 19 hours and then cooled to the internal temperature of 9° C. The crystals were collected by filtration and dried about 4 hours after the cooling was started, to give 52.37 g of polymorphic crystal (III) of donepezil hydrochloride (yield: 95.6%).

Example 12

Using a 200 L reactor can (equipped with a retreated impellor and a baffle plate) provided with a glass lining, 12.9 kg of donepezil was dissolved in 103 L of denatured ethanol by heating under stirring (linear velocity: 144 m/min). When the internal temperature reached 30° C., 3.91 kg of concentrated hydrochloric acid was added thereto. After concentrated hydrochloric acid was added, 25 g of seed crystals were added. Then, the internal temperature of the mixture was adjusted at about 25° C. 16 hours after the precipitation started, it was cooled to the internal temperature of 9° C. The crystals were collected by filtration and dried about 4 hours after the cooling was started, to give 13.19 kg of polymorphic crystal (III) of donepezil hydrochloride (yield: 93%).

The present invention is a simpler method of producing polymorphic crystal (III) of donepezil hydrochloride, which can produce the polymorphic crystal (III) directly from donepezil. Particularly, the method has high safety to environment and the bodies of operators; is gentle to environment; and can produce polymorphic crystal (III) of donepezil hydrochloride having a high refining effect at low costs.

Examples of the effect thereof will be shown below.

Experimental Example (1) Safety of the Production Method According to the Present Invention and Effect of Improving Qualities With regard to the polymorphic crystal (III) of donepezil hydrochloride obtained in Example 9, the type and amount of residual solvents were evaluated by gas chromatography. Also, the amount of the waste solvent generated in the "step of producing polymorphic crystal (III) of donepezil hydrochloride from donepezil" in Example 9 was measured. As a control test, polymorphic crystal (III) of donepezil hydrochloride was produced by the method (Control Example 1) shown below according to the method described in the publication (Example 97) of JP-A 10-53576, and the same evaluation test was conducted.

The results are shown in Table 5.

Control Example 1

500 ml of ethanol was added to 50 g of donepezil to dissolve donepezil by heating at 40° C. After cooling to room temperature, 15.05 g of concentrated hydrochloric acid was added thereto at the internal temperature of 20° C. After stirring for 9 minutes, 750 ml of isopropyl ether was added thereto at the internal temperature of 20° C. and the resulting mixture was continued stirring at room temperature for 120 minutes. Then, the precipitated crystals were collected by filtration and dried, to give polymorphic crystal (III) of donepezil hydrochloride.

TABLE 5

|  |  | Example 9 | Control Example 1 |
|---|---|---|---|
| The amount of the residual solvent | 1) Ethanol | 200 ppm | 200 ppm |
|  | 2) Isopropyl ether | — | 100 ppm |
| The amount of the waste solvent | 1) Ethanol | 400 ml | 500 ml |
|  | 2) Isopropyl ether | — | 750 ml |
|  | Total | 400 ml | 1250 ml |

The residual solvent in the polymorphic crystal (III) of donepezil hydrochloride obtained in Example 9 was only ethanol free from any safety problem, and also the amount of the solvent was as very small as 200 ppm (0.02%). On the other hand, the residual solvents in the polymorphic crystal (III) of donepezil hydrochloride obtained in Control Example 1 were 200 ppm (0.02%) of ethanol and 100 ppm (0.01%) of isopropyl ether. Isopropyl ether is classified among the "solvents for which no adequate toxicological data was found" in the ICH guide line presented in 1990's at International Conference Harmonization (ICH) concerning the medical supplies•pharmaceutical regulation harmonization in Japan, USA and Europe. It is therefore undesirable that isopropyl ether is administered as a residual solvent together with a chemical to the interior of the body of patients. In the "production method in which hydrochlorination and the crystallization of the polymolphic crystal (III) are carried out either simultaneously or successively using donepezil" other than Control Example 1 which was disclosed in JP-A 10-53576, acetone, ethyl acetate, diethyl ether, n-hexane, t-butyl methyl ether, acetonitrile, tetrahydrofuran, N,N-dimethylformamide, dimethylsulfoxide and toluene are also used besides ethanol. It is clear that like isopropyl ether of Control Example 1, these solvents will be detected as the residual solvents.

The amount of the waste solvents generated in the "step of producing polymorphic crystal (III) of donepezil crystal (III) from donepezil" in Example 9 was 400 ml of ethanol, whereas in Control Test (Control Example 1), the amount of the waste solvents was as large as 1250 ml (500 ml of ethanol and 750 ml of isopropyl ether). Isopropyl ether is highly volatile and is therefore unsuitable to working environments including the health control of operators during production steps. Also, there is a fear as to safety, for example, explosion. Also, in the "production method in which hydrochlorination and the crystallization of the polymolphic crystal (III) are carried out either simultaneously or successively using donepezil" other than Control Example 1 which was disclosed in JP-A 10-53576, a large amount of waste solvents are generated corresponding to acetone, ethyl acetate, diethyl ether, n-hexane, t-butyl methyl ether, acetonitrile, tetrahydrofuran, N,N-dimethylformamide, dimethylsulfoxide and toluene to be used similarly to the case of isopropyl ether.

In the method of producing polymorphic crystal (III) of donepezil hydrochloride according to the present invention, the residual solvents in the polymorphic crystal (III) obtained by the production method and the waste solvent generated in the course of the production are only a very small amount of ethanol. It is clear that as compared with prior art method, the method of the present invention is more improved in the safety of patients who takes the agent and operators and in the safety of working environments and also has the effect of improving qualities (reducing residual solvents).

(2) Refining Effect of the Production Method According to the Present Invention

An evaluation was conducted using high performance liquid chromatography as to the amount of donepezil hydrochloride and the amount of impurities in polymorphic crystal (III) of donepezil hydrochloride produced in the same manner as in Example 8 except that a mixture obtained by adding 0.3% (0.015 g) of 1-benzyl-4-[(5,6-dimethoxy-1-indanon)-2-ylidenyl]methylpiperidine represented by the following formula (formula 3) to 5 g (which was 1/10 the amount of donepezil used in Example 8) of donepezil was used in place of 50 g of donepezil used in Example 8, and each amount of ethanol and concentrated hydrochloric acid was decreased to 1/10 that used in Example 8. Incidentally, 1-benzyl-4-[(5,6-dimethoxy-indanon)-2-ylidenyl]methylpiperidine is an impurity which is generally produced when synthesizing donepezil.

Also, for a control test, polymorphic crystal (III) of donepezil hydrochloride was produced in the same manner as in Control Example 1 except that a mixture obtained by adding 0.3% (0.015 g) of the impurity represented by the (formula 3) to 5 g (which was 1/10 the amount of donepezil used in Control Example 1) of donepedil was used in place of 50 g of donepezil in Control Example 1 and each amount of ethanol and concentrated hydrochloric acid was decreased to 1/10 that used in Control Example 1. The same evaluation as above was conducted. The purity of the donepezil (5 g each) used in both examples was 99.55%.

The results are shown in Table 6.

(Formula 3)

|  | Example 8 | Control Example 1 |
|---|---|---|
| Donepezil hydrochloride content | 99.86% | 99.66% |
| Impurity content | 0.07% | 0.25% |

In the polymorphic crystal (III) of donepezil hydrochloride obtained in Example 8 to which the impurity (0.3%) was added, the content of the impurity was found to be decreased to 0.07%. On the other hand, in the polymorphic crystal (III) obtained in Control Example 1 to which the impurity was added, the content of the impurity was 0.25%. The contents of donepezil hydrochloride corresponded to the contents of the impurity and were respectively 99.86% and 99.66% showing that the crystals in both cases were found to differ in impurity content.

According to the method of producing the polymorphic crystal (III) of donepezil hydrochloride according to the present invention, the purity of the polymorphic crystal (III) of donepezil hydrochloride is higher than that in a prior art method, and it is therefore clear that the method of the present invention has the effect of refining donepezil.

(3) Effect of Crystallization Temperature on the Production Method According to the Present Invention The internal temperature (crystallization temperature) of the solvent during stirring after concentrated hydrochloric acid was added in the production method according to the present invention was varied, to evaluate the effects on the amount of the residual solvent (ethanol) in the polymorphic crystal (III) of donepezil hydrochloride, 90% volume cumulative diameter in the particle size distribution and yield. Specifically, polymorphic crystal (III) of donepezil hydrochloride was produced according to the following production method.

"50 g of donepezil was dissolved by stirring in 320 g (400 ml) of ethanol under heating, followed by adding 15.1 g of concentrated hydrochloric acid thereto at the internal temperature of 30° C. Then, it was cooled and continued stirring while keeping the internal temperature at 15° C., 20° C., 25° C., 30° C. or 35° C. Also after the precipitation started, the mixture was stirred for 18 hours while keeping the each internal temperature and then cooled to 9° C. Then, the crystals were collected by filtration and dried under reduced pressure for 22 hours, to give polymorphic crystal (III) of donepezil hydrochloride."

The amount of the residual solvent (ethanol) and the 90% volume cumulative diameter in the particle size distribution were evaluated using a gas chromatography apparatus and a laser diffraction particle size distribution measuring device, respectively.

The results are shown in Table 7.

TABLE 7

| the bulk temperature of the solvent during stirring (crystallization temperature) | the amount of the residual solvent (ethanol) | the 90% volume cumulative diameter in the particle size distribution | yeild (%) |
|---|---|---|---|
| 15° C. | 455 ppm | 6.9 um | 95.5% |
| 20° C. | 441 ppm | 11.9 um | 95.4% |
| 25° C. | 244 ppm | 14.3 um | 95.8% |
| 30° C. | 163 ppm | 18.2 um | 96.2% |
| 35° C. | 74 ppm | 21.7 um | 95.6% |

When the internal temperature of the solvent during stirring after concentrated hydrochloric acid was added was in a range from 15° C. to 35° C., the amount of the residual solvent was small (500 ppm or less) and the 90% volume cumulative diameter in the particle size distribution was 30 μm or less, and good qualities were therefore exhibited. However, with a rise in the internal temperature of the solvent, the amount of the residual solvent (ethanol) decreased and an increase in the 90% volume cumulative diameter in the particle size distribution was observed.

The particle size distribution of crystals is among the important factors determining the dissolving rate of the original drug and absorbing rate in vivo when the agent is administered. Generally, the smaller the particle size is, the better the dissolution rate of the original drug and the absorbing rate in vivo become. The internal temperature (crystallization temperature) of the solvent during stirring is particularly preferably 20° C. to 30° C. from viewpoint of the balance between the amount of the residual solvent (ethanol) and the particle size distribution.

It is clear that the method of producing polymorphic crystal (III) of donepezil hydrochloride according to the present invention has the effect of producing polymorphic crystal (III) of donepezil hydrochloride which is reduced in the amount of residual solvents (ethanol) and has a small 90% volume cumulative diameter in the particle size distribution in a high yield, by keeping the internal temperature (crystallization temperature) of the solvent during stirring at 15° C. to 35° C. and more preferably at 20° C. to 30° C.

The invention claimed is:

1. A method of producing a crystalline form (III) of donepezil hydrochloride (chemical name: 1-benzyl-4-[(5,6-dimethoxy-1-indanon)-2-yl]methylpiperidine• monohydrochloride) represented by the following structural formula 1:

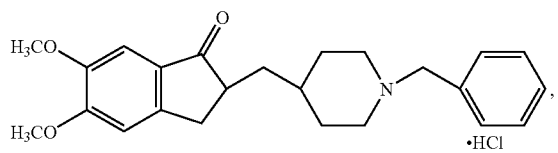

(formula 1)

by the steps of:
  dissolving donepezil (chemical name: 1-benzyl-4-[(5,6-dimethoxy-1-indanon)-2-yl]methylpiperidine) in ethanol;
  adding hydrochloric acid or hydrogen chloride thereto;
  stirring while keeping the internal temperature at 10 to 40° C.; and
  then collecting by filtration and drying the resulting crystals;

wherein the crystalline form (III) of donepezil hydrochloride is a crystalline form having peaks at the following diffraction angles (2θ) in its powder X-ray diffraction patterns;

TABLE 1

| Diffraction angle (2θ°) | Intensity (I/Io) |
|---|---|
| 6.56 | 30 |
| 9.94 | 8 |
| 13.00 | 17 |
| 15.00 | 47 |
| 15.26 | 14 |
| 15.74 | 6 |
| 16.48 | 35 |
| 17.42 | 4 |
| 18.10 | 21 |
| 18.50 | 56 |
| 19.50 | 17 |
| 20.10 | 32 |
| 20.94 | 21 |
| 21.66 | 100 |
| 22.32 | 25 |
| 22.92 | 17 |
| 23.92 | 19 |
| 24.68 | 17 |
| 26.00 | 44 |
| 27.20 | 23 |
| 28.02 | 29 |
| 28.22 | 40 |
| 28.60 | 13 | with absorption at the following wave numbers in its infrared absorption spectrum in potassium bromide: 559, 641, 648, 702, 749, 765, 786, 807, 851, 872, 927, 949, 966, 975, 982, 1007, 1034, 1071, 1080, 1111, 1119, 1131, 1177, 1190, 1205, 1217, 1230, 1250, 1265, 1292, 1313, 1367, 1389, 1420, 1438, 1453, 1461, 1470, 1500, 1589, 1605, 1697, 2407, 2419, 2461, 2624, 2641, 2651, 2667, 2837, 2848, 2873, 2924, 2954, 2961, 2993, 3007, 3377, 3433 cm$^{-1}$;

or a crystalline form having peaks at the following diffraction angles (2θ) in its powder X-ray diffraction patterns;

TABLE 2

| Diffraction angle (2θ°) | Intensity (I/Io) |
|---|---|
| 6.48 | 21 |
| 9.84 | 7 |
| 12.96 | 19 |
| 14.94 | 45 |
| 15.20 | 13 |
| 16.44 | 31 |
| 18.04 | 20 |
| 18.46 | 55 |
| 19.44 | 17 |
| 20.02 | 30 |
| 20.86 | 20 |
| 21.02 | 13 |
| 21.58 | 100 |
| 22.22 | 23 |
| 22.90 | 15 |
| 23.92 | 13 |
| 24.64 | 15 |
| 25.92 | 40 |
| 26.18 | 17 |
| 27.14 | 21 |
| 28.14 | 37 |
| 28.56 | 11 |
| 29.94 | 12 | with absorption at the following wave numbers in its infrared absorption spectrum in potassium bromide: 558.3, 641.1, 702.4, 748.5, 765.0, 786.1, 807.3, 850.8, 872.0, 926.8, 974.9, 1034.1, 1071.5, 1111.6, 1190.1, 1216.6, 1265.4, 1291.9, 1312.9, 1364.4, 1420.2, 1438.1, 1458.8, 1499.1, 1522.2, 1542.6, 1560.1, 1570.2, 1589.1, 1638.8, 1647.8, 1654.3, 1697.3, 1718.1, 1734.5, 1751.4, 1773.7, 1793.5, 1845.8, 2345.3, 2461.6, 2924.2, 3447.9 cm$^{-1}$.

2. The method of producing polymorphic crystal (III) of donepezil hydrochloride according to claim 1, wherein the amount of ethanol is 3 to 20 parts by weight to one part by weight of donepezil.

3. The method of producing polymorphic crystal (III) of donepezil hydrochloride according to claim 1, which comprises, after adding hydrochloric acid or hydrogen chloride thereto, stirring while keeping the internal temperature at 10 to 40° C.

4. The method of producing polymorphic crystal (III) of donepezil hydrochloride according to claim 3, which comprises, after adding hydrochloric acid or hydrogen chloride thereto, stirring while keeping the internal temperature at 10 to 40° C.; and, after one hour passes after crystals start precipitating, cooling to the internal temperature of 0° C. or more and less than 10° C.

5. The method of producing polymorphic crystal (III) of donepezil hydrochloride according to claim 1, wherein after hydrochloric acid or hydrogen chloride is added thereto, seed crystals of polymorphic crystal (III) of donepezil hydrochloride is added thereto in an amount of 0.01 to 10% by weight to the weight of donepezil.

* * * * *